United States Patent [19]

Thakore et al.

[11] Patent Number: 4,828,705

[45] Date of Patent: May 9, 1989

[54] PRESSURE-DEPENDENT ANISOTROPIC-TRANSPORT MEMBRANE SYSTEM

[75] Inventors: Yatin B. Thakore, East Brunswick; Karen L. Swanson; Vladimir A. Stoy, both of Princeton, all of N.J.

[73] Assignee: Kingston Technologies, Inc., Dayton, N.J.

[21] Appl. No.: 925,347

[22] Filed: Oct. 31, 1986

[51] Int. Cl.⁴ .............................................. B01D 13/00
[52] U.S. Cl. ..................................... 210/636; 210/651; 210/356
[58] Field of Search .................... 210/490, 500.43, 639, 210/409, 411, 356, 636, 651; 264/41; 427/245

[56] References Cited

U.S. PATENT DOCUMENTS

| | | | |
|---|---|---|---|
| 3,556,305 | 1/1971 | Shorr | 210/490 |
| 3,556,992 | 1/1971 | Massucco | 210/490 X |
| 3,593,852 | 7/1971 | Meriwether | 210/490 X |
| 4,095,877 | 6/1978 | Stoy et al. | |
| 4,107,121 | 8/1978 | Stoy | 264/182 X |
| 4,379,874 | 4/1983 | Stoy | 524/27 |
| 4,545,910 | 10/1985 | Marze | 210/500.43 X |
| 4,659,474 | 4/1987 | Perry et al. | 210/639 X |

Primary Examiner—Frank Spear
Attorney, Agent, or Firm—Richard C. Woodbridge

[57] ABSTRACT

Pressure-dependent anisotropic behavior is provided by a size selective separation membrane system having two successive porous layers. The first layer is a soft, elastic, effectively porous material, and the second layer is a substantially rigid porous material. When positive pressure presses the first layer against the second layer, the second layer serves as a rigid support, and the first layer is compressed to reduce its effective pore size. The first layer material is characterized by sufficient compressibility, that, when a pressure differential of 100 psi is applied across the thickness of the system, the effective flow rate is reduced by a factor of at least 20 compared to the flow rate when 100 psi is exerted in the opposite direction. A substance can be separated from a liquid mixture using the membrane system by: positioning the second layer of the membrane system in contact with the mixture; exerting pressure on the mixture to force liquid with the substance first through the pores of the rigid layer and the soft layer of the system; and reversing the flow through the membrane system by exerting pressure on the resulting filtrate, in a manner to compress the soft material sufficiently to reduce the pore size to prevent passage of the substance. The membrane system is manufactured by coagulating the layers from polymers in solution.

8 Claims, 4 Drawing Sheets

DUAL MEMBRANE APPLICATIONS

CYCLE 1
MICROFILTRATION

CYCLE 2
ULTRAFILTRATION

CYCLE 1
DEWATERING OF LARGER PROTEIN (A)

CYCLE 2
DEWATERING OF SMALLER PROTEIN (B)

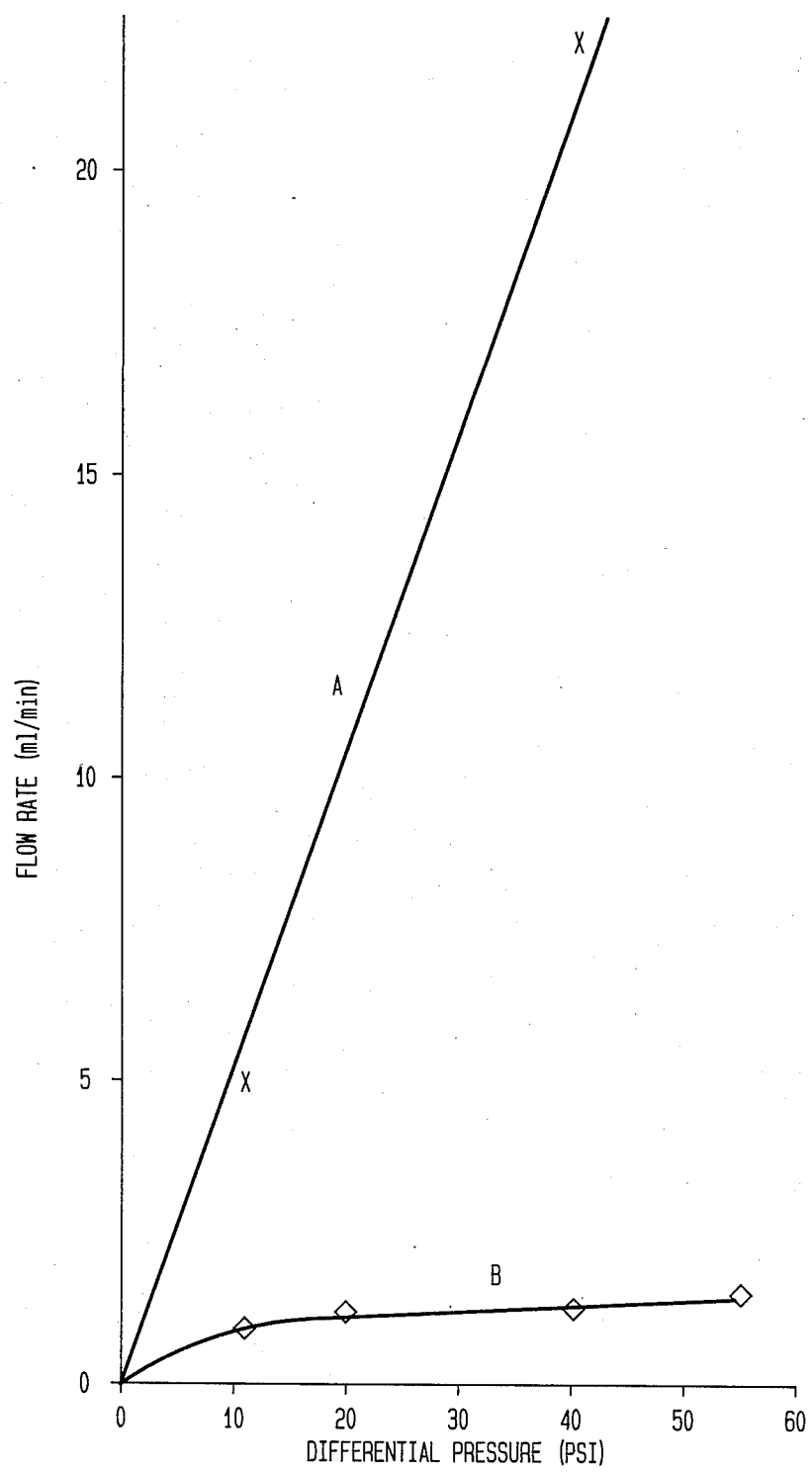

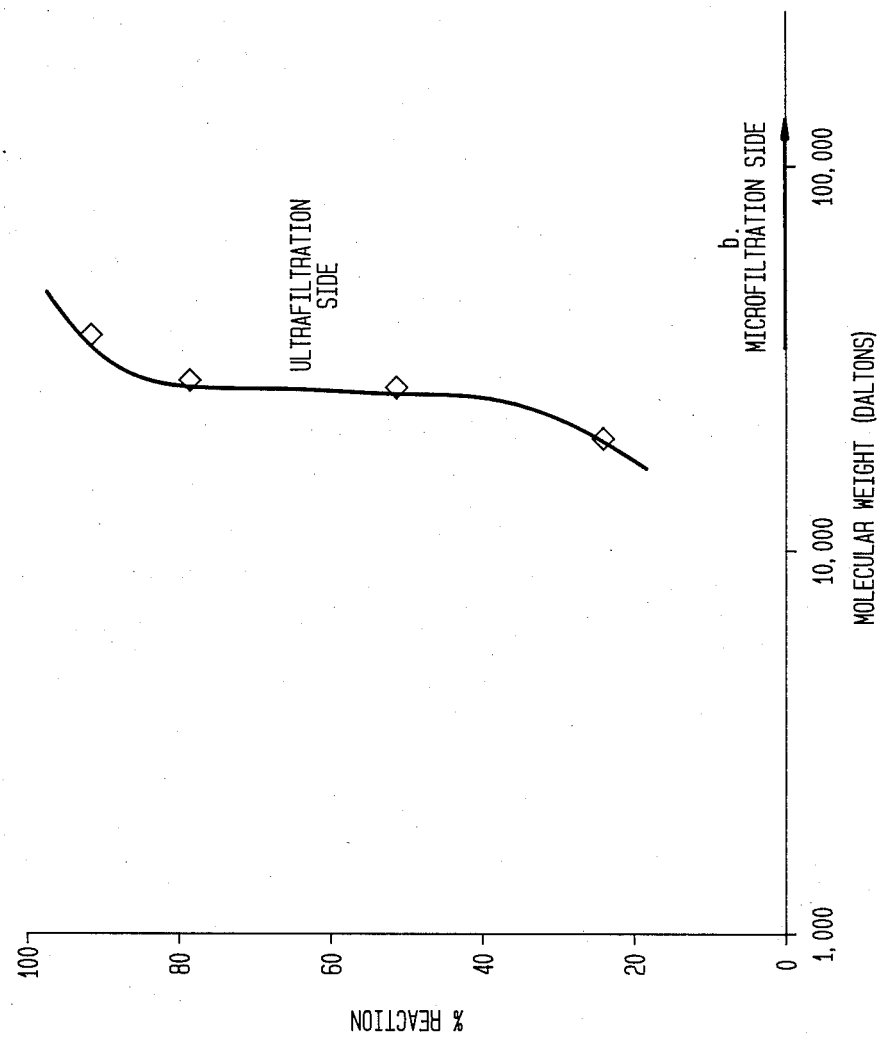

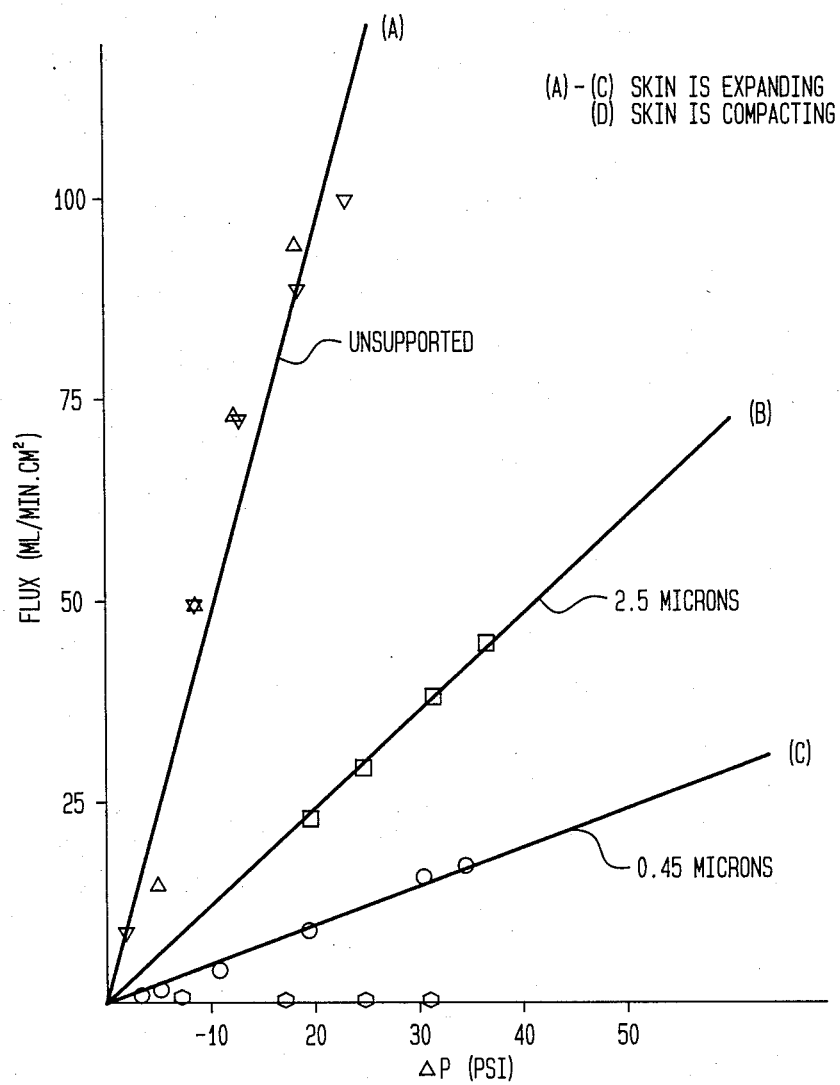

PRESSURE-DEPENDENT ANISOTROPIC-TRANSPORT MEMBRANE SYSTEM

BACKGROUND OF THE INVENTION

This invention relates to size-selective separation membranes, and to methods of manufacturing and using them.

Size-selective separation membranes selectively retain material from a feed passing through the membrane under the influence of a pressure gradient, for example, in microfiltration, ultrafiltration, or reverse osmosis. As a rule, separation membranes are produced from rigid polymers or other rigid materials to withstand the pressure driving the filtration process without compaction, and thereby to ensure that the membrane pore structure remains essentially unchanged under normal operating pressures. The flow-rate versus pressure curves using pure fluids such as water, air etc., for such membranes are essentially linear and proportional to the applied pressure, and they are inversely proportional to the controlling thickness of the membrane.

The membrane permeability values are usually rather small for membranes used for ultrafiltration and reverse-osmosis, because the pore-sizes are rather small. To achieve practical flow rates with small pore sizes, these membranes are usually asymmetric in their structure; i.e., they are composed of a thin rigid skin which has small pores controlling the flow and separation (usually <1 micron thick), supported on a porous rigid substructure. Even in this case however, the flow rate is proportional to pressure difference. The above membranes are asymmetric in terms of their morphology, but the flow-rates of the pure fluids are essentially the same and proportional to the pressure difference, irrespective of the direction of fluid flow.

Such asymmetric membranes are used with their skin sides facing the feed solution, primarily because effective "stirring" adjacent to the membrane surface is impractical in the reverse configuration. Specifically, if the feed were introduced to the more porous support side of an asymmetric membrane, it would be difficult to keep the feed well-mixed adjacent to the controlling skin, causing stagnant zones near the membrane's controlling surface and eventual build-up of high concentrations of the rejected species. This phenomenon, commonly known as concentration polarization, leads to a drastic decline in the ability of such membranes to pass fluids and retain molecules and thereby its ability to perform the intended functions is severly affected.

Concentration polarization remains a critical problem in separating large polymer molecules from a solution by ultrafiltration and, to a lesser extent, by microfiltration. The retained (rejected) solute becomes concentrated on or close to the membrane surface, and forms a gel layer which controls the transport rate. Accordingly, there have been pratical limits to the gain from improved membrane performance. Increasing the pressure only increases the thickness of the gel layer without significant increase in the flux.

Concentration polarization is currently controlled by flow management of feed-stock, which complicates the separation process and exposes solute to high shear stresses yielding a rather small actual gain in performance. Even with flow management techniques, practical fluxes are lower than the theoretical maximum, and feed-stock as well as output concentrations are limited. In addition, the energy requirements are increased. Flow management techniques are also undesirable because for many products (such as proteins) that are sensitive to shear stress.

Practical separation processes require, as a rule, several membranes of various porosities, e.g. a microfiltration membrane is used for separation of cells and other large particles from dissolved components of the fermentation broth, and subsequently an ultrafiltration membrane is used for recovering the target protein from water, salts, etc. Separate membrane modules are expensive, and the number of process components complicates the process and increases production cost.

The size-selective membranes used in microfiltration, ultrafiltration and reverse osmosis (including asymmetric membranes) generally consist of materials which are relatively rigid for the reasons given above. Examples of such rigid materials are cellulose esters, polysulfones, polyamides, polyacrylonitriles, polypropylene, polycarbonates, polytetrafluoroethylene, and derivatives of such polymers. Such membranes are available commercially from various manufacturers and suppliers, e.g. Millipore Corp. (Bedford, Mass.); Gelman Sciences Ann Arbor, Mich.; Amicon Corp. (Danvers, Mass.). The membranes are commonly prepared by phase-inversion processes, the principles of which are well-known to those in the art (see R. E. Kesting, *Synthetic Polymeric Membranes, A Structural Perspective*, 2d Ed., Wiley-Interscience, NY, N.Y.; 1985 Ch. 7, pp. 237-238.) In general, such membranes are asymmetric as to pore size, but not as to flow rate—i.e., the flow rate of pure fluid is essentially the same regardless of whether the high pressure is applied to the denser side or to the more porous side.

For example, one material that has been used for reverse osmosis membranes is cellulose acetate. Such membranes are intended to be rigid, although, as with many plastics, they may experience undesirable creep. The high-pressure side of the membrane consists of a relatively dense skin containing pores small enough to control flow. When very high pressures are applied to the opposite side of such membranes, it has been observed that the pores in the skin enlarge, allowing greater water permeation and lower salt rejection than in the normal orientation (high pressure applied to the skin side). [See, Souriraran and Matsura, *Reverse Osmosis/Ultrafiltration*, Canadian National Resourse Council (1985); and Banks and Sharples 1966 J. Appl. Chem. 16:28-32.] While the pore size enlargement in some situations is temporary, Kopeck and Sourirajan (1969) *J. Appl. Polymer Sci.* 13:637-659 propose that if very high back pressure is repeatedly applied for prolonged periods during the membrane manufacturing process, creep recovery will be incomplete and membrane pore shape will be improved. In this way, the authors suggest, product recovery will be increased without significant decrease in the membrane's ability to reject salt. Back pressure is used as part of pore shaping only during manufacture. In this pore-shaping process, the anisotropic difference in flow rates generally is below 10 in the first cycle, and is usually lower. The pressures used tend to be very high (over 600 psi). After about five cycles, the pores are permanently expanded, and the shaping process is complete. The authors also note that, over time, cellulose acetate membranes operated in the standard configuration experience undesirable compaction, apparently due to creep.

There have been other reports of asymmetric transport. Rogers et al. (1957) *Industrial and Engineering Chem.* 49(11):1933–1936 disclose a composite membrane in which the rate of water vapor permeation depends on the direction of flow. The membrane is a composite of Nylon 6 and Ethocell 610 (plasticized ethylcellulose). Such membranes, however, are not size-selective "pore-type" membranes, in the sense that their anisotropic behavior is a function of differential solubility of the permeating substance at the two membrane surfaces. The flow anisotropy with such membranes is generally small.

Nichols U.S. Pat. No. 3,846,404 discloses one specific cellulose triacetate (CTA) gel product formed from a solution by solvent replacement. CTA is dissolved in a solvent; then a gellant (i.e., a liquid that is miscible with the solvent, but is not a CTA solvent) is added. Once dry, the product is not reswollen by water. In film or capillary fiber form the product is said to be useful for various purposes including as a membrane.

SUMMARY OF THE INVENTION

One aspect of the invention features a size-selective separation membrane system comprising at least two successive porous layers. The first layer comprises a soft, elastic, effectively porous material and the second layer comprises a substantially rigid effectively porous material, e.g. one that preferably is characterized by a durometer hardness of at least about 60 and most preferably at least 75 (Shore A). When positive pressure presses the first layer against the second layer, the second layer serves as a rigid support for the first layer, and the first layer compresses to reduce its effective pore size to a desired controlling range.

In one aspect of the invention, the first layer material is characterized by a durometer hardness lower than about 50 (Shore A) and an effective pore size between about 0.001 micron and 0.1 micron when the material is in an unstressed condition. The terms "porous" and "effective pore size" include materials which do not actually have well-defined pores or holes, but which are porous due to incorporation of liquid such as water.

In a second aspect of the invention, the first layer material is characterized by sufficient compressibility that, when a pressure differential of 500 psi (and most preferably only 100 psi) is applied across its thickness, the first layer is reversibly compressed at least 10%, thereby reducing its effective pore size.

In a third aspect of the invention, the first layer material is characterized by sufficient compressibility, that, when a pressure differential of 100 psi is applied across the thickness of the system, the effective flow rate is reduced by a factor of at least 20, compared to the flow rate when 100 psi is exerted in the opposite direction.

Preferred embodiments of the invention include a number of additional features. At least in the region adjacent the first layer, the second layer is characterized by an average pore size sufficiently small (between about 0.01 micron and 200 microns) that the soft layer cannot expand into the pores of the hard layer at the interface. The first layer is a hydrogel or a porous membrane having a water content of at least 30% by weight when in contact with water. (By hydrogel, we mean a soft, flexible, aqueous-swellable polymeric material.) The first layer comprises a co-polymer of acrylonitrile and polyacrylonitrile hydrolysis products, and the second layer comprises 85–100% polyacrylonitrile. The first layer is asymmetrically porous, the pores of the first layer being smallest in a thin layer on the side of the soft material opposite the second layer. The first and second layer comprise an integral unit. The membrane system includes an external supporting mesh having openings substantially larger than the pores of the layers. The first layer is characterized by an effective pore size for microfiltration (e.g. greater than 0.02 micron) when a positive pressure is supplied to the second layer and an effective pore size for ultrafiltration (e.g. less than 0.02 micron) when a positive pressure presses the first layer against the second layer, so that the soft layer is suitable for ultrafiltration in the compressed condition.

In another aspect, the invention features separating a substance from a liquid mixture using one of the above-described membrane systems, by: positioning the second layer of the membrane system in contact with the mixture; exerting pressure on the mixture to force liquid including the substance first through the pores of the rigid layer and then through the pores of the soft layer of the membrane system; and reversing the flow through the membrane system by exerting pressure on the resulting filtrate, in a manner to compress the soft material sufficiently to reduce the pore size to prevent passage of the substance, whereby the substance is retained in the filtrate and the gel on the feed side of the membrane is disrupted.

Preferably the backflow pressure is controlled to establish an effective controlling pore size in the soft material which prevents passage of the substance but allows passage of compounds smaller than the substance. The method is particularly adapted to separate polymers, e.g., proteins from a fermentation mixture. Moreover, the method can be used to separate a substance that is too large to pass through the membrane in either direction from a polymer that passes through the membrane in one direction as described above. A particularly useful aspect of the invention features periodically reversing the pressure across the membrane system so that, when pressure is applied to the soft layer, the gel at the feed side of the system is disturbed to control concentration polarization.

A further aspect of the invention features a method of manufacturing a membrane system having a rigid polymeric layer interfacing with a polymeric layer that is soft when in contact with water, by coagulating the layers from polymers in solution.

Preferably the method of manufacture comprises providing a solution of the soft polymer and the rigid polymer in a single solvent, and contacting the solution with a bath (e.g., an aqueous liquid), one of the polymers being more soluble in the bath than the other, whereby first the less soluble polymer coagulates as a layer and then the more soluble polymer coagulates as a second layer. For example, the layers are coagulated by spreading the solution on a substrate and contacting it with the bath. Alternatively, the two polymers are provided in separate solutions, and the method comprises spreading the first solution on a substrate and coagulating it with an aqueous liquid to form a first layer, and thereafter spreading the second solution on the first layer and coagulating it with an aqueous liquid, in a manner to form adhering layers.

The membrane systems can be used to deliver a constant flow of a substance in solution by containing the solution in the membrane system, oriented with the first layer in contact with the solution. The effective pore size will vary with the amount of pressure provided to force the solution through the system, so that the flow rate of the solution is independent of pressure supplied; the pore size is selected to be maintained in a range that will allow the substance to pass, however. In medical delivery systems, for example where a medication is squeezed from the delivery system as needed, it is advantageous to provide a constant flow rate independent of pressure.

The membrane system also can be used to separate a substance from the mixture by positioning the first layer in contact with the mixture and controlling the pressure applied across the membrane system to maintain the effective pore size to exclude the substance, while passing other mixture components. For example, in ultrafiltration, pressured below 200 psi (most preferably under 100 psi) are used to achieve a controlling pore size under 0.02 microns.

The invention thus provides novel membranes with pressure-dependent anisotropic transport behavior. Specifically, by combining the physiomechanical properties of soft, elastically deformable microporous polymers with those of substantially rigid microporous membranes, the invention achieves a unique pressure-dependent diode-like behavior. The invention includes diode membranes which can be used for ultrafiltration from one side, and for the microfiltration from the other, having different flow and retention characteristics on their two sides.

As described more fully below, when separating a substance from a complex mixture, the invention enables improved control of concentration polarization, avoiding problems associated with high shear flow and depedence on the concentration gradient. The invention also enables delivery of a substance at constant flow rates with varying pressure.

Other features and advantages of the invention will be apparent from the following description of the preferred embodiments thereof.

DESCRIPTION OF THE PREFERRED EMBODIMENT

I. Drawings

FIG. 2 is a graph of pressure versus flow rate.

FIG. 3 is a graph of molecular weight versus retention.

FIG. 4 is a graph described in Example VI.

II. The Membrane System

Figure 1A:
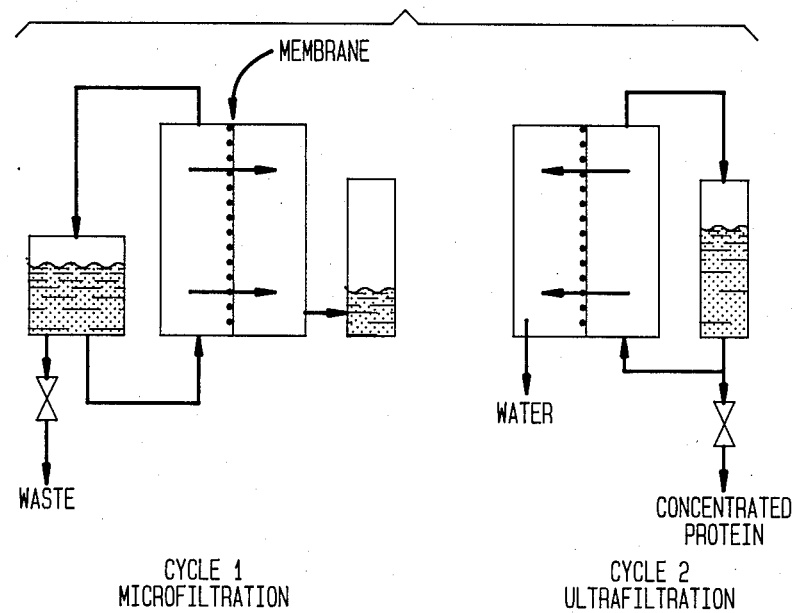
FIG. 1a is a highly diagrammatic representation of apparatus for purifying a protein.

The invention uses a pair of microporous substances, one being essentially rigid and the other being soft, elastic, and compressible.

A. The Rigid Layer

The rigid membrane layer can be made of organic polymers or of inorganic porous substances, including engineering plastics, sintered glass, raw china or burnt clay, sintered alumina, metal microfilters, e.g. such as obtained from nickel-aluminium alloys by dissolving the aluminium etc. Inorganic membranes usually need no reinforcement, but if necessary a metallic network or grid can be incorporated or placed close to them. The following organic polymers are examples: polyvinyl chloride, polyacrylonitrile, copolymers of vinyl chloride with acrylonitrile, copolymers containing predominantly acrylonitrile units, polymers and copolymers of methacrylonitrile, polymers and copolymers of vinyl acetate and vinyl propionate, polyvinyl esters and ethers and their copolymers, cyanacrylated cellulose, polymeric ethers of α-chloracrylic acid, polystyrene, solvent-soluble but water-insoluble mono-, di- and tri-esters of cellulose, regenerated cellulose, polyurethanes, polyamides and polyesters as well as their copolymers and side-substituted derivatives, polyformaldehyde and other polyacetals, polymers and copolymers of esters of acrylic and methacrylic acids, slightly hydrolyzed polyacrylonitrile in which the conversion degree of the partial hydrolysis is lower than about 5%, copolymers of vinyl chloride, polymers and copolymers of vinylidene chloride or fluoride, polymers and copolymers of vinyl carbazole polysulfones, polycarbonates and others.

B. The Soft Layer

For the soft, elastic layer, hydrogels and elastomers generally may be used. The following specific examples may be used: partially hydrolyzed polyacrylonitrile in which the conversion degree is above 5% of the acrylonitrile units, sparsely cross-linked poly-hydroxyethyl methacrylate (poly-HEMA) or acrylate, copolymers of hydroxyethyl methacrylate with alkyl acrylates and -methacrylates (alkyls with $C_1$ to $C_6$ and cross-linked with agents such as ethylene glycol or di-ethylene glycol methacrylate), polyethylene sulfonic acids and their salts, cross-linked for example with methylene-N,N bis-methacrylamide, polyvinyl alcohol sparsely cross-linked with for example melamine, glutaraldehyde, etc.; polyacrylamide sparsely cross-linked with sulfonated divinyl benzene, elastic microporous polyester-amides, polymers and copolymers of N-alkyl substituted acryl- and methacrylamides soft and/or hydrophilic polyurethanes and polymers including segmented polyurethanes, cross-linked polyethylene glycols (for example cross-linked by radiation or by reaction with di-, tri-, polyisocyanates) natural or synthetic rubbers, polysiloxanes and other elastic polymers which can be prepared in micropoous forms by known methods.

C. Manufacture and Pore Size Control

One convenient way of making a hard and soft dual membrane unit is to rely on phase separation between two rather similar polymers. The preferred system starts with a solution consisting of a combination of polyacrylonitrile with multiblock copolymers having hydrophobic acrylonitrile as the hard blocks and derivatives of hydrophilic acrylamide as the soft blocks. Under well controlled conditions a blend of these two polymers gives good phase separation, such that the skin is composed predominantly of the soft groups. Since the multiblock co-polymers can be made from a range of compositions, with varying ratios of soft and hard blocks, one can obtain varying structure and softness of the skin layer. Suitable techniques for forming the multiblock copolymers are described in Stoy et al. U.S. Pat. No. 4,095,877, Stoy U.S. Pat. No. 4,107,121, and Stoy U.S. Pat. No. 4,379,874, each of which is hereby incorporated by reference. Similar techniques can be adapted to other types of polymer systems.

A simple and effective method of manufacturing such dual membrane units comprises following steps: first, preparing a blend of two polymers, one of which is substantially rigid in contact with water and readily soluble in the solvent used, the other being soft and elastic in contact with water; second, casting the solution on a smooth surface such as on a glass plate or a metallic belt; and third, coagulating the solution in a coagulation bath capable of dissolving the solvent but incapable of dissolving the two polymers. During the immersion of the substrate with the cast polymer solution into the coagulation bath, the less soluble polymer coagulates first, forming one layer, e.g. the soft one. The more soluble polymer is driven towards the substrate, where the solvent remains still undiluted in the first phase, and precipitates, then forming the other phase, e.g. the rigid one.

Another method of preparing dual membrane units of the invention uses separate solutions of the two polymers. First one of the solutions is spread on the substrate and coagulated by an aqueous liquid, and thereafter the other polymer solution is applied onto the first polymer layer and coagulated and washed in aqueous liquids, e.g. in water. The two layers still adhere to each other, but they are more distinctly separated, with only a narrow blend interlayer.

Still another method of manufacturing the above mentioned dual membrane units consists in forming the two membrane layers separately and then laying them on each other. This method has the advantage that the soft layer can bulge under pressure of the fluid driven against the rigid layer, forming a sphere segment in which the pores are extended due to the geometry of the layer, whereby the soft membrane becomes still more permeable. In this case it is advisable to place a porous (e.g. wire net) reinforcement in the shape of a sphere segment close to the soft membrane, to protect the latter from bursting while allowing its extension.

Those skilled in the art will recognize that these methods can be modified or combined, e.g. by using saturated water vapor instead of water for polymer coagulation. Water vapors condense in such case on the polymer solution forming the desired layer.

The microporosity can be combined with macroporosity, e.g. the soft membrane layer can be made spongy by the known methods, such as by incorporating into the polymer solution a fine powder of a substance insoluble or slightly soluble in the polymer solvent, but extractable subsequently e.g. by a dilute acid or by water. Another known method of preparing microporous polymer membranes is temperature-controlled coagulation or precipitation. Still other methods are well known in the art, for example the control of the rate of precipitation by changing the composition of the coagulation or precipitation bath, etc.

A member of the "rigid" group can be combined with members of the "soft" polymer group, using known solvents, preferably at least partly water-miscible ones, and coagulating or precipitating the polymer layers with nonsolvent liquids.

The pore size depends primarily on the rate at which the solvent is replaced by the non-solvent and can be controlled, in broad limits, by temperature and by using appropriate blends of the solvent with a non-solvent for precipitation. Still another means for achieving a desired pore size consists of polymerizing monomers having higher solubility in a solvent than that of the resulting polymer or copolymer in the same solvent, so that, during the cross-linking and/or polymerization, the polymer slowly coagulates, and the excess solvent separates in the form of very small droplets, forming a porous and spongy matrix. The higher the surplus of the solvent, the larger the size of the pores. The appropriate pore size of the rigid layer is such that, when the soft layer or membrane is forced against it under pressure, the soft layer does not penetrate too deeply and permanently into the pores of the hard layer. The rigid porous layer generally needs no further support, i.e., it is self-supported.

It is clear that the two layers have different functions, and they need not be joined in one sheet. On the contrary, in many cases it is more convenient to manufacture separately two different membranes which are then used together, forming a system with the above mentioned reinforcing substrates. Such an arrangement allows easier replacement of a damaged part and avoids undesired internal stresses or wrinkling, so that the two membranes can shrink and swell independently. Even when each layer has its own support, the two layers are considered one unit or entity, since the benefits of the invention are obtained only if the two membranes or layers are used in series, together. This holds even when a third reinforcing support is placed between the two membranes.

D. Flow Characteristics

Preferably, the soft membrane layer is denser, so that its resistance contributes the major pressure drop for a given flow. The soft (as well as the rigid) layer is formed by a network of pores, characterized by certain values of pore cross section, length and tortuosity, which determine flow and separation characteristics of the membrane. If the pressure is applied from the soft side, the soft porous layer is compressed against its rigid counterpart, and its porosity and pore cross-sectional area decrease, whereas the tortuosity and the average pore length increase. Once compressed, the soft layer behaves as a more dense membrane with lower flow and better retention. If the flow direction is reversed, the soft membrane layer expands under the pressure gradient into the free space, and its average pore cross-sectional area increases while tortuosity decreases. The net effect is higher flow through, and lower retention by, the softer rate-controlling layer in the direction of flow. If the soft layer is unattached to the rigid layer, then it expands, increasing its active area and decreasing the thickness, so that the flow rate increases considerably and progressively with applied pressure. Moreover, in the expanded state, pore cross section increases in the same proportion as overall area.

The pore size for microfiltration is usually in the range of 0.02 microns (200A) to 10 microns (100,000A), and the pressure differential is generally under 100 psi. For ultrafiltration, in which the pressure differential employed is generally under 200 psi (and most preferably under 100 psi), the pore size is between a little over 0.0001 microns (1 A) and 0.02 microns (200 A), so that the latter value can be considered the limiting one as between the pore size of the rigid and soft layer of the present membranes. As a practical matter, there may be some overlapping. If the pore sizes of the two membranes are chosen in the above ranges, the present membrane system can be used for microfiltration, when the feed is provided from the rigid side, or for ultrafiltration, if the flow direction is reversed.

In one example, when the soft hydrogel-type membrane is in the compaction mode against the porous rigid support, the flux at 30 psi is 0.2 ml/min-cm$^2$ with the effective pore size in 0.01–0.03 micron range. When the pressure direction is reversed, however, the hydrogel is in the expansion mode and the flux at 30 psi is 140 ml/min-cm$^2$ and the effective pore size is greater than 10 microns. The difference between the flowrates is 700-fold at 30 psi and higher at higher pressures.

For the best utilization of the asymmetric flow characteristics of the membrane, it is advisable to leave sufficient room for the expansion of the soft layer if the fluid is fed from the rigid layer side. This can be achieved in three different ways:

(1) The membrane is unsupported from its soft side, while pressure is controlled so that it does not exceed the burst strength of the membrane, either as a whole (if both layers are connected), or of its flexible layer (if disconnected). In this way maximum flux for a given pressure is achieved;

(2) The membrane is supported only if extended to a certain degree which is safely below the limit of the membrane strength. This can be achieved by a porous plate, grid or net which is properly shaped to accommodate the extended membrane and leaves a certain free space between the soft layer and itself, into which the flexible layer expands. This arrangement is advantageous because it permits increase in area and decrease in thickness of the flexible layer, and allows separations at higher pressures.

(3) The soft layer is supported by a porous layer, the porosity of which is substantially higher than that of the membrane layers (e.g., wire mesh, or paper filter on a rigid porous support). Such a highly porous support allows the soft membrane to expand on micro-scale into the pores of such support even if its overall deformation is restricted.

III. Use of the Membrane System

A. Protein Recovery From Fermentation Broth

The above-described ultra/micro-filtration configuration can be advantageously utilized, for example, in protein isolation and concentration from a mixture containing larger species (such as cells, cell debris and larger soluble polymers) as well as from smaller species (low molecular solutes, electrolytes and water).

As shown in FIG. 1a, in the first step, the fermentation broth is fed from the rigid side of the membrane acting as a microfiltration membrane and therefore retaining particulates, cells and very high molecular weight polymers but readily allowing the transport of moderate sized proteins, water and small solutes. In the second step, the direction of the pressure gradient is reversed, so that the protein is retained, while water, electrolytes, etc. are removed, thus concentrating and purifying the protein. This process can be carried out in a batch mode or continuously in a cyclic manner either on a small laboratory scale or industrial scale. The utilization of both sides of the membrane provides significant capital savings and automatic backflushing, as described below.

Figure 1B:
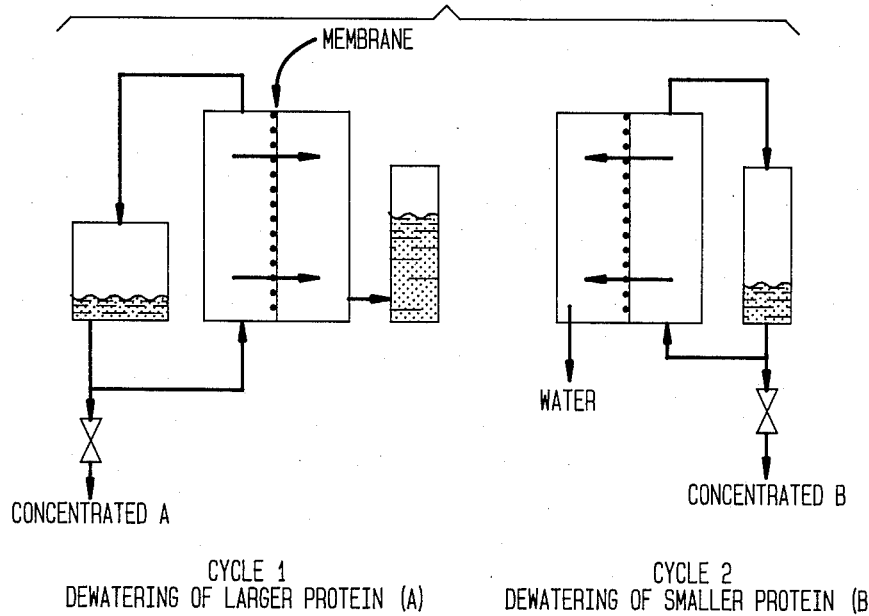
FIG. 1b is a highly diagrammatic representation of apparatus for separating a larger protein from a smaller protein.

As shown in FIG. 1b, the same membrane can be used to separate polymers (e.g. proteins) of different sizes. The membrane has a larger cut-off from left side and smaller cut-off from right side. In cycle 1, feed consisting of two proteins is fed on the left side. The retentate is the concentrated Protein A (larger protein). The filtrate is then fed from the opposite side in cycle 2 and concentrated protein B (smaller protein) is collected as retentate.

With this arrangement, therefore, the dual functions of microfiltration and ultrafiltration are performed using the same diode-like membrane module.

For separating fractions of macromolecular compounds, it is also possible to arrange two such dual membranes symmetrically in series, with rigid layers facing outwards. The feed enters from the rigid side of first system, and the filtrate from the first system passes through the soft side of the second system. The first system will remove the largest particles or molecules, the second the smallest ones. The desired fraction accumulates between the two systems, the ions and the small molecules flow through the soft layer even in its compacted state.

B. "Backflushing" to Alleviate Concentration Polarization

One can use the above-described module in a manner such that functions of cycles 1 and 2 are not carried to completion but only to partial completion, such that the left side and the right side are alternatively used, with the time of each cycle adjusted according to flow characteristics. This mode of operation will destabilize the polarized layers adjacent to the membrane and, at the same time, perform the microfiltration or ultrafiltration functions. The use of the two sides this way also amounts to backflushing one side while the other side is being used. Such membranes therefore could provide an added dimension to polarization control and for keeping the surfaces "clean".

If the flow is reversed in relatively fast cycles (e.g., at least every 15 minutes and faster where conditions require) before concentration polarization can be fully developed, the separation can proceed at much higher flow rates and efficiency. The dual membrane systems with separate and highly extensible soft layers are particularly advantageous for this type of polarization control because of the periodical changes in area on the gel-layer sides. The gel deposits are disintegrated and removed during a short back-flush at a relatively low pressure. The disruption can be achieved with substantially no backflow of components that are being passed through the membrane system.

C. Constant Flow Rate

If the soft, compacting layer of the membrane is designed so that, even under compaction, it allows a small flow, then the membrane system of the invention can be used in a device that dispenses a constant flow rate, independent of pressure. The analogy in solid-state diodes is that of a zener diode which is used in a reverse fashion to provide a constant output irrespective of the applied voltage.

Such membranes could be used as constant dosage devices or on-demand drug delivery systems. Since, in the compression mode, the flow-rate is virtually independent of pressure, a subcutaneously implanted delivery system can be squeezed from outside for a fixed time to give predictable drug delivery.

IV. Examples

The following examples are non-limiting.

Example I

Polyacrylonitrile (PAN), m.w. 150.000, was partially hydrolyzed so that 30% of acrylonitrile units were converted to acrylamide groups, 12 g of the multiblock-copolymer thus obtained, in dry condition (after coagulating in water, washing, drying and grinding) and 6 g of non-hydolyzed polyacrylonitrile of the same molecular weight were dissolved in 176 g of the dimethyl sulfoxide and the fresh, clear solution, cast at 20° C. on a glass plate, spread with a casting knife with a spacing of 375 microns, and immediately coagulated at 20° C. in deionized water to give a fibrous-looking membrane. This membrane was washed several times in water and the flow rates and cut-offs were measured in a 10 ml stirred ultrafiltration cell, the tested liquid being fed first from one side and then from the other side of the membrane using pressurized nitrogen. A Whatman #41 filter paper was used as support underneath the membrane.

The membrane side exposed to air in the casting process was the soft one, and its surface was dull. The side adhering to the glass was the rigid one, with glossy surface. Apparently, the hydrophilic block-copolymer, which is less soluble in dimethyl sulfoxide, coagulated first, while the more soluble PAN accumulated mostly at the bottom where at first the solvent was still undiluted.

The flow rates of deionized water were as follows:
A. when water was fed from the soft side:

| at 11 psi | 0.17 ml/min-cm$^2$ |
| 20 psi | 0.23 ml/min-cm$^2$ |
| 40 psi | 0.31 ml/min-cm$^2$ |
| 55 psi | 0.34 ml/min-cm$^2$ |

B. water fed from the rigid side:

| 11 psi | 1.09 ml/min-cm$^2$ |
| 40 psi | 4.99 ml/min-cm$^2$ |

The molecular weight cut-offs based on studies of globular proteins were as follows:

Feeding from the soft side, the cut-off was at about 35,000, while the test with feeding from the rigid side did not show any protein retention of gamma-globulin (M.W. 167,000)

The unique nature of the membranes is illustrated by the curves in FIG. 2 showing that the microfiltration side (A) allows 17 times faster flow than the opposite side (B) at 40 PSI. (Membrane diameter was 25 mm). In FIG. 3, the ultrafiltration side of the dual membrane shows a sharp cut-off at about 30,000 daltons (represented by diamonds). The opposite microfiltration side of the same membrane however lets even $\gamma$-globulin (160,000 daltons) pass through without any retention (represented by triangles).

Example II 5 g of the copolymer from the Example I and 5 g of nonhydrolyzed PAN were dissolved in 90 g dimethylsulfoxide, and the clear solution was cast on a glass plate and spread with a casting knife, with a spacing of 375 microns. The solution layer was immediately coagulated at 20° C. in deionized water. The membrane thus formed had fibrous texture, with dull air-side and shiny glass-side. The thoroughly washed membrane was tested for flow-rates as disclosed in Example I.

Flow rates in deionized water
A. Water fed from the soft side:

| 11 psi | 2.23 ml/min-cm$^2$ |

-continued

| 20 psi | 2.68 ml/min-cm$^2$ |
| 40 psi | 2.96 ml/min-cm$^2$ |

B. Water fed from the rigid side:

| 11 psi | 3.80 ml/min-cm$^2$ |
| 20 psi | 7.24 ml/min-cm$^2$ |
| 40 psi | 20.93 ml/min-cm$^2$ |

Very different pressure-dependence is noticeable.

Example III

Multi-block copolymer of acrylonitrile with 55 mol. % of acrylamide was dissolved to a 10% concentration in 55% aqueous solution of sodium rhodanide at 20° C. The solution was poured on a glass plate at 20° C. with a doctor knife spacing of 100 microns, whereafter a microporous poly-tetrafluorethylene membrane with a pore rating of 2–5 microns (Zitex ® fine grade by Norton Chemplast) was laid onto the solution layer and the whole system was coagulated in deionized water and washed.

The composite dual membrane, in which Zitex ® was the rigid component, was then tested for the flow-rates as shown in the foregoing Examples:
A. Water fed from the soft side:

| 12.5 psi | 0.0067 ml/min-cm$^2$ |
| 21 psi | 0.0109 ml/min-cm$^2$ |

Water fed from the rigid side:

| (a) | 10 psi | 2.45 ml/min-cm$^2$ |
| (b) | 11 psi | 0.48 ml/min-cm$^2$ |

The membrane used in (a) is self-supporting without the filter paper. When the soft side was not hindred by the filter paper, the flow rate increased 365 times, while with the filter paper as a support (as in (b)), it increased only 71 times as compared to the flow rate from the other side.

From the Example it is evident that the role of the compressibility of the soft layer, and its extensibility in reversed position, are significant.

Example IV

A plate of sintered glass, fine grade, was used as the rigid layer. The soft layer, consisting of a 250 micron thick membrane of a multi-block copolymer of acrylonitrile and acrylamide with 65% water-swellability, displaying a rubber-like elastically, was laid onto the rigid layer. The soft membrane was protected by a nickel wire-net, in the shape of a sphere segment allowing the membrane to be blown up to a half of the radius of the sphere. The membrane was slightly stretched in the relaxed state to avoid shrinking. The system had similar diode-like characteristics as those of the foregoing Examples.

Example V

A membrane consisting of multiblock copolymer of polyacrylonitrile-acrylamide (MW 150,000, 55% acrylamide groups) was cast from 5% solution by weight in dimethylsulfoxide onto a rigid Polyester non-woven fabric (Hollytex TM 3396, 9 mils thick, Filtration Sciences Corpn; Mount Hollysprings, Pa.). The thickness of the soft cast membrane was 5 mils. The soft layer was supported by 2 mil-thick non-woven polyester fabric (Hollytex TM 3310). The membrane was found to be diode like. The flow rate from the rigid side was over 400 times higher than flow rate from soft side at 30 psi.

Example VI

A solution made with the same multiblock copolymer and concentration as Example V was cast over a glass plate and the skin was supported by a 2 mil thick non-woven polyester fabric (Hollytex TM 3310) by placing it onto the polymer solution before coagulation in water. A series of rigid supports were placed under the backside of the membrane (non-skin side; side which coagulated against glass) and pressure was applied to the skin side. Water fluxes were as follows (at 10 psi):

| Soft layer against: (Pressure against soft layer) | Flux (ml/min-cm$^2$) |
| --- | --- |
| Whatman 41 | 0.31 |
| Whatman 50 | 0.14 |
| Hollytex TM 3396 | 0.15 |
| MSI TM nylon 0.45 μm membrane | 0.06 |
| DynaWeb TM DW918 | 0.07 |

Pressure was then applied to the backside without any hard support. The flow rate at 10 psi was now 48.8 ml/min-cm$^2$ and the difference in flow rate between sides was 100–800 times. In addition, pressure was applied to the hard support placed against the backside (non-skin side). Water fluxes were then less than 49.8 ml/min-cm$^2$ at 10 psi, because the hard support absorbed some of the pressure drop. Fluxes at 10 psi are listed below.

| Approx. Pore Size | Soft layer against: (Pressure against hard layer) | Flux (ml/min-cm$^2$) |
| --- | --- | --- |
| 20–25 μm | Whatman 41 | 33 |
| 2.7 μm | Whatman 50 | 5.6 |
| 30–40 μm | Hollytex 3396 | 42 |
| 0.45 μm | MSI TM nylon 0.45 mm membrane | 4.8 |
| 2.5 μm | DynaWeb TM DW918 | 11 |

FIG. 4 is a graph depicting the above results.

Example VII

The membrane of example VI was placed against the MSI TM nylon 0.45 mm membranes as in Example VI. Blue dextran (0.01–0.03 mm) under 10–20 psi of pressure was placed against the skin side and over 90% was retained. Conversely, blue dextran under 10–20 psi of pressure was not retained when placed against the hard rigid layer.

Other embodiments are within the following claims. For example, the dual membrane system can be in configurations other than a flat sheet; specifically, the dual membrane system can be configured as a hollow fiber, a tube, or a folded sheet.

We claim:

1. A method of separating a substance from a fluid mixture by using a pressure-dependent anisotropic-transport membrane system, comprising the steps of:
   (a) positioning said fluid mixture in contact with a rigid layer of an effectively porous component of a pressure-dependent anisotropic-transport membrane system;
   (b) exerting a pressure gradient across said pressure-dependent anisotropic-transport membrane system, whereby:
      (i) said pressure gradient causing a higher pressure to act against said rigid layer to force said fluid containing said substance through said rigid layer,
      (ii) said pressure gradient causing a lower pressure on the other side of said rigid layer, said pressure gradient acting on a soft elastic layer of reversibly compressible and effectively porous component of said pressure-dependent anisotropic-transport membrane system, said pressure gradient causing said soft elastic layer to reversibly expand away from said rigid layer to increase the effective pore size of the soft elastic layer and allow the fluid containing the substance to pass through the soft elastic layer,
   (c) reversing the pressure gradient across the pressure-dependent anisotropic-transport membrane system, said reversed pressure gradient causing a higher pressure to be exerted against the elastic layer, reversibly compressing the soft elastic layer against the rigid layer reducing the effective pore size of the soft elastic layer sufficiently to allow the passage of the fluid through the soft elastic layer and then through the rigid layer, but preventing the passage of the substance through the soft elastic layer,
   whereby the substance is retained on the side of the soft elastic layer.

2. The method recited in claim 1, wherein step (c) of reversing said pressure gradient further includes controlling said pressure gradient exerted across the soft elastic layer to a predetermined range which maintains an effective pore size in the soft elastic layer and prevents the passage of said substance through the soft elastic layer but allows passage of any other substance smaller than said substance through the soft elastic layer.

3. The method recited in claim 2, wherein said mixture includes a second substance too large to pass through the membrane system in either direction, whereby said method effectively separates said first substance from said second substance.

4. The method recited in claim 1, wherein the pressure gradient across said pressure-dependent anisotropic-transport membrane system is periodically reversed, whereby during application of a higher pressure to said soft elastic layer said fluid flowing through said pressure-dependent anisotropic-transport membrane system disrupts the build-up of substance on said rigid layer, and whereby during application of higher pressure to said rigid layer said fluid flowing through said pressure-dependent anisotropic-transport membrane system disrupts the build-up of substance on said soft elastic layer.

5. A method for manufacturing pressure-dependent anisotropic-transport membrane system having a rigid substantially porous polymeric layer interfacing with a soft elastic substantially porous reversibly compressible polymeric layer, comprising the steps of:
   (a) dissolving a soft elastic polymer and a rigid polymer in solvent;
   (b) coagulating said polymers by contacting the solution with a fluid bath in which one of the polymers is more soluble than the other polymer, whereby the first, less soluble polymer coagulates as a first layer and a second more soluble polymer coagulates as a second layer.

6. The method of claim 5, wherein said fluid bath is an aqueous fluid.

7. The method of claim 6, wherein the layers are coagulated by spreading the solution on a substrate and then contracting the substrate with said fluid bath.

8. The method of claim 5, further comprising the steps of:

(a) dissolving said first polymer in a first solution,
(b) dissolving said second polymer in a second solution,
(c) spreading the first solution on a substrate and coagulating the first solution with a non-solvent of said first polymer to form a first layer, and
(d) spreading the second solution on the first layer and coagulating the second solution with a non-solvent of said second polymer to form adhering layers of the first and second polymers.

* * * * *